United States Patent [19]

Watson et al.

[11] Patent Number: 4,886,911

[45] Date of Patent: Dec. 12, 1989

[54] HERBICIDAL CYCLOHEXANE-1,3-DIONE DERIVATIVES

[75] Inventors: Keith G. Watson, Blackburn; Craig G. Lovel, North Fitzroy, both of Australia

[73] Assignee: ICI Australia Limited, Melbourne, Australia

[21] Appl. No.: 61,306

[22] Filed: Jun. 12, 1987

[30] Foreign Application Priority Data

Jul. 1, 1986 [AU] Australia .............................. PH6674

[51] Int. Cl.$^4$ ........................................... C07C 131/00
[52] U.S. Cl. ................................... 564/221; 548/550; 548/548; 546/243; 71/94; 71/95; 71/111; 564/218; 564/219; 564/220
[58] Field of Search ............... 564/221, 218, 219, 220; 71/105

[56] References Cited

U.S. PATENT DOCUMENTS

| | | | |
|---|---|---|---|
| 2,984,673 | 5/1961 | Bortnick et al. | 71/95 |
| 3,541,111 | 11/1970 | Gevike et al. | 71/95 |
| 4,652,303 | 3/1987 | Watson et al. | 71/88 |
| 4,692,553 | 9/1987 | Keil et al. | 564/185 |

FOREIGN PATENT DOCUMENTS

| | | |
|---|---|---|
| 0133349 | 2/1985 | European Pat. Off. . |
| 0169521 | 7/1985 | European Pat. Off. . |
| 02116052 | 5/1987 | European Pat. Off. . |
| 2137200 | 3/1984 | United Kingdom . |

*Primary Examiner*—David B. Springer
*Attorney, Agent, or Firm*—Cushman, Darby & Cushman

[57] ABSTRACT

The invention concerns compounds of formula I wherein:

X and Y are independently selected from the group consisting of hydrogen, $C_1$ to $C_4$ alkyl, $C_1$ to $C_4$ haloalkyl, and the group wherein X and Y together from a three or four-membered carbon bridge the bridge optionally comprising one or both of a double bond and a carbonyl group;

Z is selected from the group consisting of hydrogen, halogen, $C_1$ to $C_4$ alkyl and $C_1$ to $C_4$ alkanoyl;

$R^1$ is selected from the group consisting of: hydrogen; an acyl group; and an inorganic or organic cation;

$R^2$ is selected from the group consisting of: $C_1$ to $C_6$ alkyl; $C_2$ to $C_6$ alkenyl; $C_2$ to $C_6$ haloakenyl; $C_2$ to $C_6$ alkynyl; and substituted $C_1$ to $C_6$ alkyl wherein the alkyl group is substituted with a substituent selected from the group consisting of halogen, phenyl, and substituted phenyl wherein the benezene ring is substituted with from one to three substituents selected from the group consisting of halogen, and $C_1$ to $C_6$ alkyl;

$R^3$ is selected from the group consisting of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

The compounds are herbicides and in further embodiments the invention provides processes for the preparation of compounds of formula I, herbicidal compositions comprising the compounds of formula I and processes for severly damaging or killing unwanted plants by application of compounds of formula I.

5 Claims, No Drawings

HERBICIDAL CYCLOHEXANE-1,3-DIONE DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Patent No. 464 655 and its equivalents such as UK Patent No. 1 461 170 and U.S. Pat. No. 3,950,420.

A variety of herbicidal compounds containing substituted phenyl cyclohexane-1,3-diones are described in the art. For example, French Patent No. 2,518,990, as well as the published British Patent application equivalent thereto, viz., No 2,116,544 describes various 5-(4-substituted phenyl) cyclohexane-1,3-diones and European Patent Application 085,529 describes various 5-(polysubstituted phenyl) cyclohexane-1,3-diones and their herbicidal properties.

It has now been found that a new group of cyclohexan-1,3-dione derivatives which have a 5-mesityl substituent which is in turn substituted with an amidomethyl amino group, exhibit exceptionally high general grass-killing activity.

Accordingly the invention provides a compound of formula I

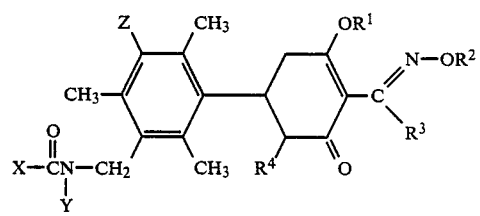

wherein:

X is selected from the group consisting of hydrogen, $C_1$ to $C_4$ alkyl, and $C_1$ to $C_4$ haloalkyl;

Y is selected from the group consisting of hydrogen, $C_1$ to $C_4$ alkyl, and $C_1$ to $C_4$ alkanoyl;

OR X AND Y form a three or four-membered carbon bridge which may include one double bond and one carbonyl group;

Z is selected from the group consisting of hydrogen, halogen, $C_1$ to $C_4$ alkyl, and $C_1$ to $C_4$ alkanoyl;

$R_1$ is selected from the group consisting of: hydrogen; an acyl group; and an inorganic or organic cation;

$R_2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; and substituted $C_1$ to $C_6$ alkyl wherein the alkyl group is substituted with a substituent selected from the group consisting of halogen, phenyl, and substituted phenyl wherein the benzene ring is substituted with from one to three substituents selected from the group consisting of halogen, and $C_1$ to $C_6$ alkyl;

$R_3$ is selected from the group consisting of: $C_1$ to $C_6$ alkyl; and $R_4$ is selected from the group consisting of: hydrogen; $C_1$ to $C_6$ alkyl; and ($C_1$ to $C_6$ alkoxy) carbonyl.

When in the compound of formula I $R^1$ is chosen from acyl the nature of the acyl group is not narrowly critical. Although not intending to be bound by theory, it is believed that when $R^1$ is acyl and acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alky, $C_1$ to $C_6$ haloalkyl, $C_1$ to $C_6$ alkoxy and Chd 1 to $C_6$ alkylthio.

When in the compound of formula I $R^1$ is chosen from an inorganic or organic cation the nature of the cation is not narrowly critical. Although not intending to b bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^5R^6R^7R^8N^\oplus$ wherein $R^5$, $R^6$, $R^7$ and $R^8$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C^1$ to $C_6$ alkoxy and $C_1$ to $C_6$ alkylthio.

The compounds of the invention may exist in two isomeric forms as shown below, wherein $\phi$ represents the group

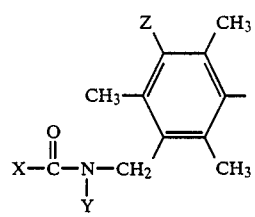

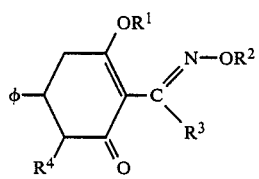

Ia

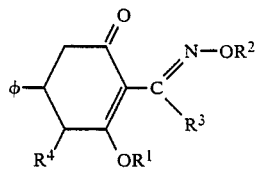

Id

It should be recognized that when R¹ is hydrogen the compounds of the invention may exist in any one of four tautomeric forms as shown below wherein φ represents the group

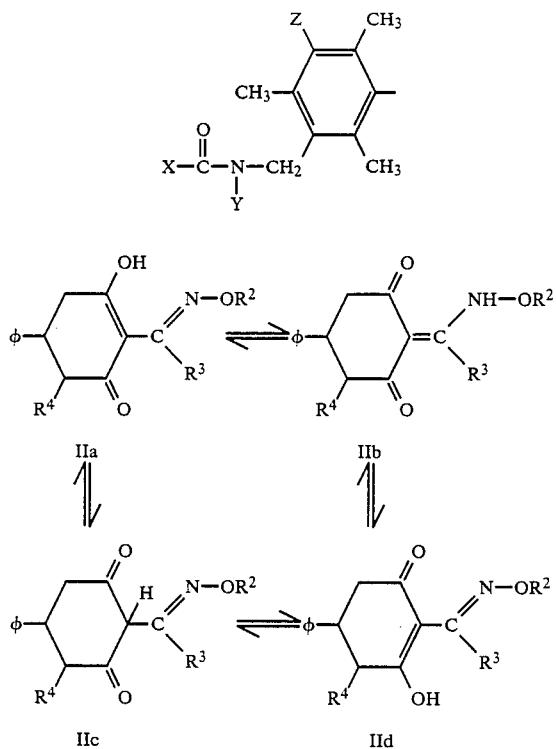

Preferred compounds of the invention include those compounds of formula I wherein:

X is selected from hydrogen, methyl, trifluoromethyl and chloromethyl;

Y is selected from hydrogen and methyl;

OR X and Y together form one of the bridging groups—

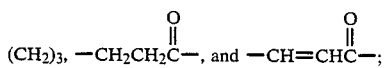

Z is selected from hydrogen, methyl, acetyl, propionyl and butyryl;

R¹ is selected from hydrogen, the alkali metal cations, $C_2$ to $C_6$ alkanoyl, benzoyl and substituted benzoyl wherein the benzoyl ring is substituted with from one to three substituents chosen from halogen, nitro and cyano;

R² is selected from methyl, ethyl, n-propyl, allyl, propargyl and 3-choroallyl;

R³ is selected from methyl, ethyl and n-propyl;

R⁴ is hydrogen.

Specific examples of the compounds of the invention include those compounds detailed in Table 1 below.

TABLE 1

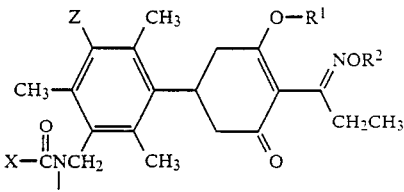

| Compound No | X | Y | Z | R¹ | R² |
|---|---|---|---|---|---|
| 1 | CH₃ | H | H | H | C₂H₅ |
| 2 | ClCH₂ | H | CH₃CO | H | C₂H₅ |
| 3 | CCl₃ | H | H | H | C₂H₅ |
| 4 | H | CH₃ | H | H | C₂H₅ |
| 5 | CCl₃ | H | CH₃CO | H | C₂H₅ |
| 6 | CF₃ | H | H | H | C₂H₅ |
| 7 | —(CH₂)₃— | | H | H | C₂H₅ |
| 8 | —CH=CHCO— | | H | H | C₂H₅ |
| 9 | CF₃ | H | CH₃ | H | CH₂CH=CH₂ |
| 10 | CF₃ | H | CH₃ | Na | CH₂CH=CH₂ |

The compounds of the invention may be prepared by a variety of methods and in a further aspect the invention provides methods for the preparation of compounds of formula I.

Conveniently the preparation of the invention can be considered in four or five parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX.

(ii) reacting, preferably in the presence of a base, an aldehyde derivative of formula V with an acetic acid ester of formula IVc to give a 2-arylalkenoate derivative of formula VIc which is in turn reacted, preferably in the presence of a base, with an acetoacetic acid ester derivative of formula VIIc to give an intermediate of formula VIIIa which may be isolated or hydrolysed directly, preferably in the presence of an acid, to give a 5-arylcyclohexan-1,3-dione of formula IX.

Part B involves the acylation of a compound of formula IX to give a 2-acylcyclohexane-1,3-dione derivative of formula Xa. Alternatively Part B involves the acylation of a compound of formula VIIIa or VIIIb to give a 2-acylcyclohexane-1,3-dione derivative of formula XIa or XIb respectively which may be hydrolysed, preferably in the presence of a base, to give a 2-acylcyclohexane-1,3-dione of formula Xa. The acylation reaction may be carried out by reacting a cyclohexane-1,3-dione derivative of formula VIII or IX with:

(i) an acid anhydride of formula XII in the presence of either an alkali metal salt of the corresponding acid of formula XV or an alkoxide salt of formula XIV, wherein M is an alkali metal ion and R is $C_1$ to $C_6$ alkyl; or
(ii) an acid anhydride of formula XII in the presence of the corresponding acid of formula XV, preferably in the presence of a Lewis acid or strong proton acid catalyst; or
(iii) with an alkali or alkaline earth metal hydride followed by reaction with an acid anhydride of formula XII or an acid halide of formula XVI; or
(iv) an acid anhydride of formula XII in the presence of a strong organic base such as 4-dimethylaminopyridine or imidazole.

Alternatively, this acylation reaction may be carried out by:
(v) reacting a cyclohexane-1,3-dione derivative of formula VIII or formula IX with an acid halide of formula XVI in the presence of a base to give an intermediate O-acyl derivative of the type of formula XVII; and
(vi) reacting the intermediate of formula XVII with a Lewis acid or strong proton acid catalyst; or
(vii) reacting the intermediate of formula XVII with a suitable strong organic base such as 4-dimethylaminopyridine.

Part C involves the reaction of a compound of formula Xa by electrophilic aromatic amidomethylation to give a compound of formula Xb.

Part D involves the formation of a compound of the invention of formula I wherein $R^1$ is hydrogen, that is a compound of formula II. This reaction may be carried out either by reacting a 2-acyl cyclohexane-1,3-dione of formula Xb with:
(i) an alkoxyamine derivative of formula XVIII, or
(ii) hydroxylamine to give an intermediate oxime derivative of formula XIX and reacting that intermediate oxime derivative of formula XIX with an alkylating agent of formula XX, wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part E involves the formation of a compound of the invention of formula I wherein $R^1$ is a substituent other than hydrogen.

Compounds of the invention of formula I, wherein $R^1$ forms an acyl derivative of a compound of formula II, may be prepared from the corresponding compounds of the invention of formula II by reacting with an acylation reagent of formula XXI, wherein L is a leaving group preferably a halogen.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively, the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:
reacting a 2-acylcyclohexane-1,3-dione derivative of formula Xb with an alkoxyamine derivative of formula XVIII to give a compound of the invention of formula II or reacting the 2-acylcyclohexane-1,3-dione derivative of formula Xb with hydroxylamine and alkylating the oxime intermediate of formula XIX with an alkylating agent of formula XX, wherein L is a leaving group, to give a compound of the invention of formula II; and optionally
reacting the compound of the invention of formula II with a compound of formula XXI wherein L is a leaving group, to give a compound of the invention of formula I.

Certain of the intermediate compounds of formula Xb are novel compounds and therefore in further embodiments the invention provides novel compounds of formula Xb and processes for the preparation thereof. The structures of the compounds described above are detailed on the following pages.

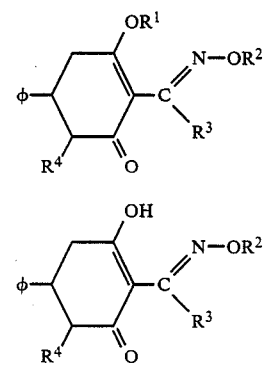

I

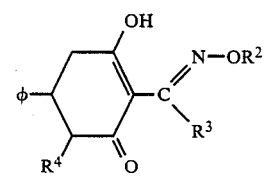

II $CH_3COCH_3$     IVa
$CH_3COCH_2R^4$     IVb
$CH_3CO_2R$     IVc

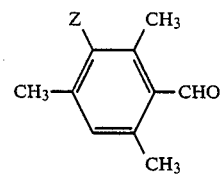

V

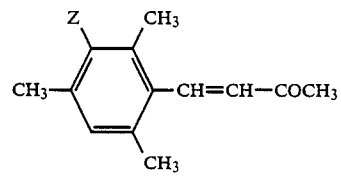

VIa

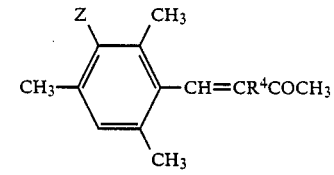

VIb

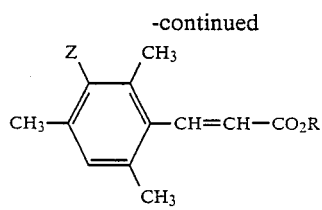

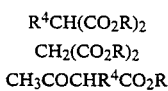

R⁴CH(CO₂R)₂   VIIa
CH₂(CO₂R)₂   VIIb
CH₃COCHR⁴CO₂R   VIIc

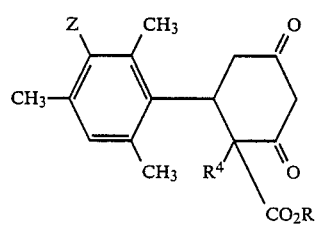
VIIIa

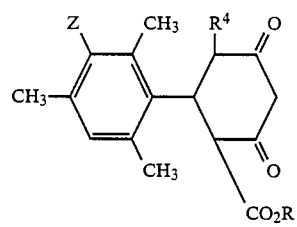
VIIIb

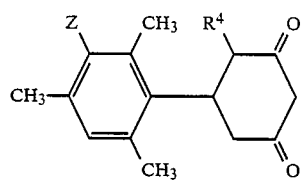
IX

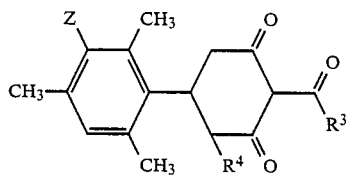
Xa

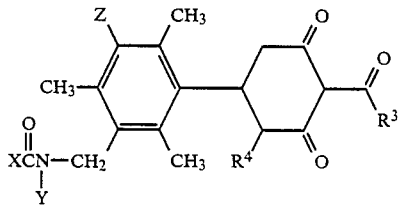
Xb

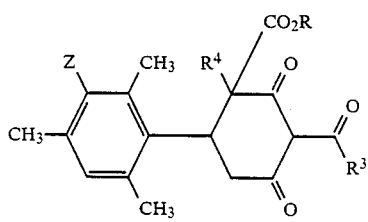
XIa

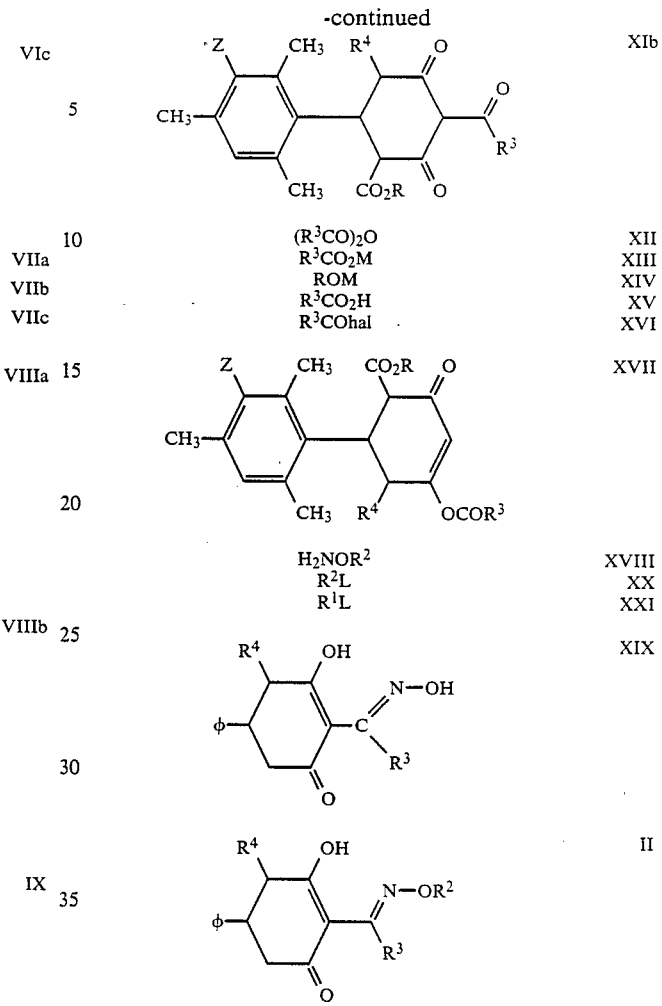

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against monocotyledonous plants, dicotyledonous plants being relatively unaffected by rates of application of the compounds of the invention which are severely damaging or lethal to most grass species.

Accordingly, in yet a further aspect the invention provides a process for controlling monocotyledonous weeds in cultivated crops, which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severly damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an inert carrier therefor.

Certain of the compounds of formula I exhibit useful plant growth regulating activity. For example, while compounds of formula I are selectivity active herbicides against wild grasses in crops of cultivated plants at some rates of application they exhibit plant growth regulating effects in said crops.

Plant growth regulating effects may be manifested in a number of ways. For example, increasing the sugar content of plants, suppression of apical dominance, stimulation of auxiliary bud growth, stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley, and increasing the sugar content of sugar cane.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 1 ppm to 99% by weight of the active ingredient. Dilute compositions ready for use preferably contain 1 ppm to 2% of active ingredient, while concentrated compositions may contain from 20 to 99% of active ingredient, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powders or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

The rate of application of the compounds of the invention will depend on a number of factors including, for example, the compound chosen for use, the identity of the plants to be treated, the formulations selected for use and whether the compound is to be applied for foliage or root uptake. As a general guide, however, an application rate of from 0.001 to 10 kilograms per hectare is suitable while from 0.01 to 5 kilograms per hectare may be preferred.

The compositions of the invention may comprise, in addition to one or more compounds of the invention, one or more compounds not of the invention but which possess biological activity. For example, as hereinbefore indicated the compounds of the invention are effective herbicides against monocotyledonous weeds, wild grasses, but have little or no herbicidal effect against dicotyledonous plants, broad-leaved plants.

As a result, in certain applications where it is desired to protect a crop against both wild grasses and broad-leaved weeds it may be preferred to use a herbicidal composition comprising a mixture of at least one herbicidal compound of formula I as hereinbefore defined and at least one other herbicide active against broad-leaved weeds.

The invention is now illustrated by but in no way limited to the following Examples.

EXAMPLE 1

2-[1-(Ethoxyimino)propyl]-3-hydroxy-5-[3-acetyl-5-(N-chloroacetyl-aminometh)-2,4,6-trimethylphenyl)]-cyclohex-2-en-1-one (2)

(i) N-hydroxymethylchloroacetamide (0.19 g) was added to a cooled, stirred solution of 2-propionyl-3-hydroxy-5-(3-acetyl-2,4,6-trimethylphenyl) cyclohex-2-en-1-one (0.50 g) in a mixture of acetic acid (2.5 ml) and concentrated sulfuric acid (1 ml). The mixture was stirred at 20° C. for one hour, poured into water and extracted with methylene chloride (2×100 ml). The combined methylene chloride layers were dried (MgSO$_4$) and evaporated to give the crude product (0.55 g). Purification by elution through silica gel with ethyl acetate-methylene chloride gave recovered starting material and then 2-propionyl-3-hydroxy-5-[3-acetyl-5-(N-chloroacetylaminomethyl)-2,4,6-trimethylphenyl] cyclohex-2-en-1-one (0.15 g, 24%). The product was characterized by proton magnetic resonance spectroscopy (CDCl3; in ppm): 1.18 (3H,t); 2.21(3H,s); 2.27(3H,s); 2.42(3H,s); 2.47 (3H,s); 2.4–3.9(7H,m); 4.02(2H,s); 4.50(2H,d); 6.6(1H,s); 18.0(1H,s).

(ii) Sodium acetate (0.09 g) and ethoxyamine hydrochloride (0.11 g) were added to a solution of 2-propionyl-3-hydroxy-5-[3-acetyl-5-(N-chloroacetylaminomethyl)-2,4,6-trimethylphenyl)] cyclohex-2-en-1-one (0.40 g) in ethanol (10 ml) at room temperature. The solution was stirred for 18 hours at 20° C. and then the solvent was removed under reduced pressure and the residue was dissolved in chloroform and washed with water. The organic layer was dried (MgSO$_4$) and concentrated under reduced pressure to give 2-[1-(ethoxyimino)-propyl]-3-hydroxy-5-[3-acetyl-5-(N-chloroacetylaminomethyl)-2,4,6-trimethylphenyl] cyclohex-2-en-1-one (2) as a pale yellow oil. The compound was characterised by its behaviour on thin-layer chromatography and by its proton nuclear magnetic resonance spectrum, details of which are recorded in Table 2, Example 2.

EXAMPLE 2

The immediate precursors for compounds Nos 1,3,4,5,6,7,8 and 9 were each prepared by amidomethylation of the appropriate 2-propionyl-5-mesitylcyclohexane-1,3-dione derivative with the appropriate N-hydroxymethylamide following essentially the procedure as described in Example 1 part (i). The final compounds were then prepared by reaction with ethoxyamine or allyloxyamine following the method given in Example 1, part (ii). Each compound was characterised primarily by its proton magnetic resonance spectrum and details are recorded in Table 2 below.

TABLE 2

| Compound No. | Proton Chemical Shift in ppm (CDC13) |
|---|---|
| 1 | 1.19(3H,t); 1.33(3H,t); 1.96(3H,s); 2.31(3H,s); 2.38(6H,s); 2.3–3.9 (7H,m); 4.12(2H,q); 4.43(2H,d); 5.2(1H,bs); 6.89(1H,s); 15.1(1H,bs) |
| 2 | 1.18(3H,t); 1.34(3H,t); 2.22(3H,s); 2.27(3H,s); 2.42(3H,s); 2.47(3H,s); 2.3–3.9(7H,m); 4.02(2H,s); 4.13(2H,q); 4.50(2H,d); 6.61(1H,bs); 15.1(1H,bs) |
| 3 | 1.19(3H,t); 1.33(3H,t); 2.34(3H,s); 2.39(6H,s); 2.3–4.0(7H,m); 4.12 (2H,q); 4.56(2H,d); 6.57(1H,bs); 6.91(1H,s); 15.0(1H,bs) |
| 4 | 1.18(3H,t); 1.33(3H,t); 2.26(6H,s); 2.40(3H,s); 2.65(3H,d); 2.40–4.0 (7H,m); 4.13(2H,q); 4.57(2H,d); 6.91 (1H,s); 8.09(1H,d); 15.1(1H,bs) |
| 5 | 1.18(3H,t); 1.34(3H,t); 2.26(3H,s); 2.41(3H,s); 2.43(3H,s); 2.48(3H,s); 2.3–4.0(7H,m); 4.13(2H,q); 4.56 (2H,d); 6.84(1H,bs); 14.9(1H,bs) |
| 6 | 1.18(3H,t); 1.33(3H,t); 2.34(3H,s); 2.39(6H,s); 2.4–3.9(7H,m); 4.12 (2H,q); 4.54(2H,d); 6.90(1H,s); 6.9 (1H,bs); 15.0(1H,bs) |
| 7 | 1.18(3H,t); 1.33(3H,t); 1.95(2H,m); 2.27(6H,s); 2.35(3H,s); 2.2–4.0(11H,m); 4.12(2H,q); 4.54(2H,s); 6.88(1H,s); 15.0(1H,s) |
| 8 | 1.19(3H,t); 1.33(3H,t); 2.35(6H,s); 2.39(3H,s); 2.3–4.0(7H,m); 4.12(2H,q); 4.71(2H,s); 6.64(2H,s); 6.88(1H,s); OH not observed |
| 9 | 1.13(3H,t); 2.20(3H,s); 2.28(3H,s); 2.33(3H,s); 2.36(3H,s); 2.3–4.0(7H,m); 4.55(4H,2xd); 5.2–6.0(3H,m) 6.1(1H, broad exchangeable) |

EXAMPLE 3

Compound No. 10, the sodium salt of compound No. 9 was prepared as follows:

To a solution of 2-[1-(allyloxyimino) propyl]-3-hydroxy-5-[3-trifluoroacetylamidomethyl-2,4,5,6-tetra methylphenyl]cyclohex-2-en-1-one (200 mg) in acetone (10 ml) was added a solution of sodium hydroxide (20 mg) in water (1 ml). The mixture was stirred briefly at room temperature and then concentrated on a rotary evaporator to give the sodium salt (10) as an orange foam (220 mg).

EXAMPLE 4

This non-limiting Example illustrates the preparation of formulations of the compounds of the invention.

(a) Emulsifiable Concentrate

Compound No 1 was dissolved in toluene containing 7% v/v "Teric" N13 and 3% v/v "Kemmat" SC15B to give an emulsifiable concentrate which was diluted with water to the required concentration to give an aqueous emulsion which was applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No 2 (5 parts by weight and "Dyapol" PT (1 part by weight) were added to a 2% aqueous solution (94 parts by weight) of "Teric" N8 and the mixture was ball milled to produce a stable aqueous suspension which may be diluted with water to the required concentration to give an aqueous suspension which may be applied by spraying.

("Dyapol" is a Trade Mark and "Dyapol" PT is an anionic suspending agent; "Teric" N8 is a product of ethoxylation of nonylphenol.)

(c) Emulsifiable Concentrate

Compound No 1 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying.

("Solvesso" is a Trade Mark and "Solvesso" 150 is a high boiling point aromatic petroleum fraction.)

(d) Dispersible Powder

Compound No 1 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns.

("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) Dusting Powder

Compound No 1 (10 parts by weight), attapulgite (10 parts by weight) and pyrophyllite (80 parts by weight) were thoroughly blended and then ground in a hammermill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 4 and 6, in the evaluation of the pre-emergence and post-emergence herbicidal activity of the compounds.

EXAMPLE 5

The pre-emergent herbicidal activity of the compounds of the invention formulated as described in Example 4 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 3

Pre-emergent Herbicidal Activity

| Compound No | Application Rate kg/ha | Wh | Jm | Rg | Ot | B | P | Ip | Ms | Sf |
|---|---|---|---|---|---|---|---|---|---|---|
| 1 | 1.0 | 5 | 5 | 5 | 5 | 5 | 0 | 0 | 0 | 0 |
| 1 | 0.25 | 3 | 5 | 4 | 4 | 3 | — | — | — | — |
| 2 | 1.0 | 3 | 4 | 5 | 4 | 3 | 0 | 0 | 0 | 0 |
| 3 | 1.0 | 4 | 5 | 5 | 5 | 5 | 0 | 0 | 0 | 0 |
| 4 | 1.0 | 4 | 5 | 5 | 5 | 5 | 0 | 0 | 0 | 0 |
| 4 | 0.25 | 2 | 5 | 5 | 5 | 3 | — | — | — | — |
| 5 | 1.0 | 4 | 5 | 5 | 4 | 4 | 2 | 0 | 0 | 0 |
| 6 | 1.0 | 5 | 5 | 5 | 5 | 4 | 2 | 1 | 3 | 0 |
| 6 | 0.25 | 1 | 5 | 5 | 5 | 2 | — | — | — | — |
| 7 | 1.0 | 5 | 5 | 5 | 4 | 4 | 0 | 0 | 0 | 0 |
| 7 | 0.25 | 2 | 4 | 4 | 3 | 0 | — | — | — | — |
| 8 | 1.0 | 1 | 5 | 4 | 0 | 0 | 0 | 0 | 0 | 0 |
| 9 | 1.0 | 5 | 5 | 5 | 5 | 4 | 4 | 3 | 3 | 3 |
| 9 | 0.25 | 4 | 4 | 4 | 4 | 4 | — | — | — | — |
| 10 | 1.0 | 4 | 5 | 5 | 4 | 1 | 0 | 0 | 0 | 0 |

EXAMPLE 5

The post-emergent herbicidal activity of the compounds of the invention formulated as described in Example 4 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 4

Post-emergent Herbicidal Activity

| Compound No | Application Rate kg/ha | Wh | Jm | Rg | Ot | B | P | IP | Ms | Sf |
|---|---|---|---|---|---|---|---|---|---|---|
| 1 | 1.0 | 5 | 5 | 5 | 5 | 5 | 0 | 0 | 0 | 0 |
|   | 0.25 | 5 | 5 | 5 | 5 | 5 | — | — | — | — |
|   | 0.0625 | 5 | 5 | 5 | 5 | 5 | — | — | — | — |
| 2 | 1.0 | 5 | 5 | 5 | 5 | 5 | 0 | 0 | 0 | 0 |
|   | 0.25 | 5 | 5 | 3 | 4 | 4 | — | — | — | — |
|   | 0.0625 | 5 | 3 | 2 | 2 | 2 | — | — | — | — |
| 3 | 1.0 | 5 | 5 | 5 | 5 | 5 | 0 | 0 | 0 | 0 |
|   | 0.25 | 4 | 5 | 5 | 5 | 5 | — | — | — | — |
|   | 0.0625 | 0 | 5 | 3 | 4 | 3 | — | — | — | — |
| 4 | 1.0 | 5 | 5 | 5 | 5 | 5 | 0 | 0 | 0 | 0 |
|   | 0.25 | 5 | 5 | 5 | 5 | 5 | — | — | — | — |
|   | 0.0625 | 5 | 5 | 5 | 5 | 5 | — | — | — | — |
| 5 | 1.0 | 5 | 5 | 5 | 5 | 5 | 0 | 0 | 0 | 0 |
|   | 0.25 | 5 | 5 | 5 | 5 | 5 | — | — | — | — |
|   | 0.0625 | 4 | 5 | 4 | 5 | 5 | — | — | — | — |
| 6 | 1.0 | 5 | — | 5 | 5 | 5 | 2 | 4 | 4 | 0 |
|   | 0.25 | 5 | — | 5 | 5 | 5 | — | — | — | — |
|   | 0.0625 | 4 | — | 5 | 5 | 5 | — | — | — | — |
| 7 | 1.0 | 5 | 5 | 5 | 5 | 5 | 0 | 0 | 0 | 0 |
|   | 0.25 | 4 | 5 | 5 | 5 | 5 | — | — | — | — |
|   | 0.0625 | 3 | 5 | 1 | 5 | 5 | — | — | — | — |
| 8 | 1.0 | 1 | 4 | 3 | 4 | 0 | 0 | 0 | 0 | 0 |
| 9 | 1.0 | 4 | 5 | 4 | 5 | 5 | 4 | 3 | 5 | 3 |
|   | 0.25 | 4 | 5 | 4 | 4 | 5 | — | — | — | — |
|   | 0.0625 | 2 | 3 | 1 | 2 | 4 | — | — | — | — |
| 10 | 1.0 | 2 | 5 | 4 | 4 | 5 | 0 | 0 | 0 | 0 |

EXAMPLE 6

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 5 below. Damage to test plants was assessed after 14 days on a scale of 0 to 5 where 0 is 0 to 20% damage and 5 is complete kill. The degree of herbicidal damage was assessed by comparison with untreated control plants. The results are given in Table 5 below. A dash (—) means that no experiment was carried out.

The names of the test plants were as follows:

| | |
|---|---|
| Mz | Maize |
| Ww | Winter wheat |
| Rc | Rice |
| Br | Barley |
| Av | *Avena fatua* |
| Dg | *Digitaria sanquinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |

TABLE 5

| Compound No. | Application Rate kg/ha | TEST PLANT | | | | | | | | | | |
|---|---|---|---|---|---|---|---|---|---|---|---|---|
| | | Mz | Ww | Rc | Br | Av | Dg | Al | St | Ec | Sh | Ag |
| 1 | 0.2 | 5 | 4 | 3 | 5 | 5 | 5 | 5 | 5 | 5 | 4 | 5 |
| 1 | 0.1 | 4 | 4 | 2 | 5 | 5 | 5 | 5 | 4 | 5 | 4 | 4 |
| 1 | 0.05 | 2 | 4 | 1 | 4 | 5 | 4 | 4 | 4 | 5 | 4 | 2 |
| 2 | 0.4 | 4 | 3 | 1 | 3 | 4 | 4 | 3 | 3 | 5 | 3 | 1 |
| 2 | 0.2 | 3 | 0 | 1 | 0 | 3 | 4 | 2 | 1 | 3 | 1 | 0 |
| 3 | 0.2 | 3 | 0 | 2 | 4 | 4 | 2 | 3 | 3 | 5 | 4 | 2 |
| 3 | 0.1 | 3 | 0 | 0 | 3 | 4 | 3 | 4 | 2 | 4 | 4 | 0 |
| 4 | 0.2 | 4 | 4 | 4 | 4 | 4 | 5 | 4 | 4 | 5 | 5 | 4 |
| 4 | 0.1 | 3 | 2 | 4 | 4 | 4 | 4 | 5 | 4 | 5 | 5 | 3 |
| 4 | 0.02 | 4 | 3 | 1 | 4 | 4 | 4 | 4 | 2 | 4 | 2 | 1 |
| 5 | 0.2 | 5 | 4 | 4 | 5 | 5 | 4 | 4 | 5 | 5 | 5 | 2 |
| 5 | 0.1 | 3 | 2 | 4 | 4 | 4 | 4 | 4 | 4 | 5 | 4 | 0 |
| 6 | 0.2 | 4 | 4 | 4 | 5 | 5 | 5 | 5 | 5 | 5 | 5 | 4 |
| 6 | 0.05 | 4 | 3 | 0 | 4 | 4 | 4 | 4 | 5 | 5 | 4 | 3 |
| 7 | 0.1 | 3 | 2 | 3 | 4 | 4 | 4 | 4 | 4 | 4 | 3 | 2 |
| 7 | 0.05 | 3 | 2 | 3 | 4 | 4 | 4 | 4 | 4 | 4 | 4 | 1 |
| 8 | 0.2 | 4 | 0 | 3 | 3 | 4 | 4 | 4 | 4 | 4 | 3 | 1 |
| 8 | 0.1 | 4 | 0 | 2 | 0 | 2 | 3 | 2 | 3 | 3 | 0 | 1 |

We claim:

1. A compound of formula I

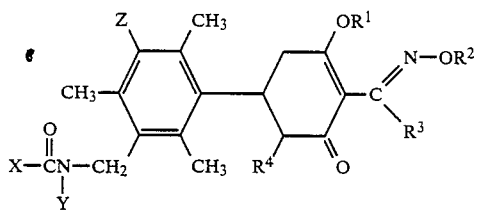

wherein:

X and Y are independently selected from the group consisting of hydrogen, $C_1$ to $C_4$ alkyl, and $C_1$ to $C_4$ haloalkyl;

Z is selected from the group consisting of hydrogen, halogen, $C_1$ to $C_4$ alkyl and $C_1$ to $C_4$ alkanoyl;

$R_1$ is selected from the group consisting of: hydrogen; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; and substituted $C_1$ to $C_6$ alkyl wherein the alkyl group is substituted with a substituent selected from the group consisting of halogen, phenyl, and substituted phenyl wherein the benzene ring is substituted with from one to three substituents selected from the group consisting of halogen, and $C_1$ to $C_6$ alkyl;

$R^3$ is selected from the group consisting Of: $C_1$ to $C_6$ alkyl; and $R^4$ is selected from the group consisting of: hydrogen; $C_1$ to $C_6$ alkyl; and ($C_1$ to $C_6$ alkoxy) carbonyl.

2. A compound according to claim 1 wherein in the formula I:

$R^1$ is selected from the group consisting of: hydrogen; $C_2$ to $C_6$ alkanoyl; benzoyl; substituted benzoyl wherein the benzene ring is substituted with from one to three substituents selected from the group consisting of hydrogen, nitro, cyano, $C_1$ to $C_6$ alkyl, $C_1$ to $C_6$ haloalkyl, $C_1$ to $C_6$ alkoxy and $C_1$ to $C_6$ alkylthio; alkali and alkaline earth metal ions; transition metal ions; ammonium; tri- and tetra(alkyl)ammonium ions wherein alkyl is selected from $C_1$ to $C_6$ alkyl and $C_1$ to $C_6$ hydroxyalkyl; and wherein the substituents $R^2$, $R^3$, $R^4$, X, Y and Z are as defined according to claim 1.

3. A compound according to claim 1 wherein in the formula I:

X is selected from hydrogen, methyl, trifluoromethyl and chloromethyl,

Y is selected from hydrogen and methyl, $R^1$ is selected from the group consisting of hydrogen, the alkali metal cations, $C_2$ to $C_6$ alkanoyl, benzoyl and substituted benzoyl wherein the benzoyl ring is substituted with from one to three substituents chosen from halogen, nitro and cyano;

$R^2$ is selected from methyl, ethyl, n-propyl, allyl, propargyl and 3-chloroallyl;

$R^3$ is selected from methyl, ethyl, and n-propyl;

$R^4$ is hydrogen.

4. A compound according to claim 1 wherein in formula I:

X is selected from hydrogen, methyl, trifluoromethyl and chloromethyl,

Y is selected from hydrogen and methyl, $R^1$ is selected from hydrogen and sodium;

$R^2$ is selected from ethyl and allyl;

$R^3$ is ethyl;

$R^4$ is hydrogen.

5. A compound according to claim 1 selected from the group consisting of
2-[1-(Ethoxyimino)propyl]-3-hydroxy-5-[3-acetyl-5-(N-chloroacetyl-aminomethyl)-2,4,6-trimethylphenyl]-cyclohex-2-en-1-one.

2-[1-(Ethoxyimino)propyl]-3-hydroxy-5-[3-(N-acetyl-aminomethyl)-2,4,6-trimethylpheny]cyclohex-2-en-1-one;

2-[1-(Ethoxyimino)propyl]-3-hydroxy-5-[3-(N-trichloroacetyl-aminomethyl)-2,4,6-trimethylphenyl]-cyclohex-2-en-1-one;

2-[1-(Ethoxyimino)propyl]-3-hydroxy-5-[3-(N-formyl-N-methyl-aminomethyl)-2,4,6-trimethylphenyl]cyclohex-2-en-1-one;

2-[1-(Ethoxyimino)propyl]-3-hydroxy-5-[3-acetyl-5-(N-trichloroacetyl-aminomethyl)-2,4,6-trimethyl-phenyl]cyclohex-2-en-1-one;

2-[1-(Ethoxyimino)propyl]-3-hydroxy-5-[3-(N-trifluoro-acetyl-aminomethyl)-2,4,6-trimethylphenyl]-cyclohex-2-en-1-one;

2-1[1-(allyloxyimino)propyl]-3-hydroxy-5-3-(N-trifluoroacetyl-aminomethyl)-2,4,5,6-tetramethyl-phenyl]cyclohex-2-en-1-one.

* * * * *